United States Patent
Dahl et al.

(10) Patent No.: US 6,772,015 B2
(45) Date of Patent: Aug. 3, 2004

(54) BIFURCATED LEAD SYSTEM FOR A CARDIAC VEIN

(75) Inventors: Roger Dahl, Andover, MN (US); Elisabeth Lacy Belden, Maple Grove, MN (US)

(73) Assignee: Medtronic, Inc, Minneapolis, MN (US)

( * ) Notice: Subject to any disclaimer, the term of this patent is extended or adjusted under 35 U.S.C. 154(b) by 455 days.

(21) Appl. No.: 09/820,156

(22) Filed: Mar. 28, 2001

(65) Prior Publication Data

US 2002/0143380 A1 Oct. 3, 2002

Related U.S. Application Data (60) Provisional application No. 60/258,769, filed on Dec. 29, 2000.

(51) Int. Cl.[7] .................................................. A61N 1/05
(52) U.S. Cl. ........................ 607/122; 607/125; 600/374; 600/381
(58) Field of Search .............................. 607/122, 117, 607/115, 116, 129, 123, 125; 600/373, 374, 381, 393

(56) References Cited

U.S. PATENT DOCUMENTS

| | | | | |
|---|---|---|---|---|
| 4,458,677 A | * | 7/1984 | McCorkle, Jr. | 607/123 |
| 4,641,656 A | * | 2/1987 | Smits | 607/5 |
| 4,643,201 A | | 2/1987 | Stokes | 128/786 |
| 5,144,960 A | | 9/1992 | Mehra et al. | 128/786 |
| 5,503,158 A | | 4/1996 | Coppock et al. | 128/696 |
| 5,628,779 A | | 5/1997 | Bornzin et al. | 607/123 |
| 5,769,881 A | | 6/1998 | Schroeppel et al. | 607/123 |
| 6,544,270 B1 | * | 4/2003 | Zhang | 606/129 |

OTHER PUBLICATIONS

LeClercq, C. et al., "Acute Hemodynamic Effects of Biventricular DDD Pacing in Patients With End–Stage Heart Failure," *JACC*, vol. 32, No. 7, p. 1825–31 (Dec. 1998).

* cited by examiner

*Primary Examiner*—Thor Campbell
(74) *Attorney, Agent, or Firm*—Girma Wolde-Michael; Daniel G. Chapik (57) ABSTRACT

A bi-furcated medical electrical lead that is adapted to be implanted in the cardiac venous system is disclosed. The lead includes a bifurcated distal portion having first and second elongated members, or fingers. In one embodiment, the first elongated member, or thumb portion, is adapted to be positioned within the coronary sinus or great cardiac vein. The second elongated member, or finger portion, of the bifurcated distal tip, may be positioned within a branch vessel of the coronary sinus such as the posterior vein or middle cardiac vein. The thumb portion may carry at least one electrode for pacing and/or sensing, and may carry additional electrodes for multi-polar pacing applications, whereas the finger portion may carry a defibrillation electrode. Portions of the pacing/sensing electrodes may be insulated so that electrical stimulation is only delivered to myocardial tissue. According to one method of using the bifurcated lead system, the lead may be employed in conjunction with a standard right ventricular pacing and defibrillation lead to deliver big-ventricular pacing and defibrillation therapy. Both the thumb and finger may include preformed or shapeable distal tips to aid in the positioning of these structures within the respective vessels. A stiffening member may be used to maintain the thumb in a substantially parallel position with the finger when the lead is being positioned within the vascular system, as may be accomplished with the further use of a guide catheter.

30 Claims, 5 Drawing Sheets

BIFURCATED LEAD SYSTEM FOR A CARDIAC VEIN

RELATED APPLICATIONS

This Application claims priority to provisionally-filed U.S. Patent Application Serial No. 60/258,769 filed Dec. 29, 2000 entitled "Bifurcated Lead System for a Cardiac Vein", which is incorporated herein by reference in its entirety.

FIELD OF THE INVENTION

The present invention generally relates to medical electrical leads; and, more specifically, to a bifurcated lead system designed for big-ventricular pacing and defibrillator from within two branches of a cardiac vein.

BACKGROUND OF THE INVENTION

It has become common to provide electrical stimulation to a patient's heart by positioning multiple medical electrical leads at various locations within the cardiac system. For example, a first lead may be positioned within the right atrium of the heart for pacing and sensing of the right atrium. A second lead may be positioned within the right ventricle for pacing and sensing of the right ventricle.

Several problems exist when multiple leads are positioned within the heart or associated vascular system. Generally, both leads will be introduced into the heart through a common location as through the superior venal cave. Movement of one lead with respect to the other lead at this common entry location may cause dislodgement of one or both of the leads. Additionally, if the leads are in close proximity to one another, relative movement of the leads causes the lead insulation to wear, and may result in lead failure.

One manner of addressing the above-described problems involves providing a single, bifurcated lead system. This type of lead system includes a first portion, or "finger", of the lead that that is generally adapted for placement in the right atrium. A second portion, or "finger", of the lead is designed to be advanced within the right ventricle. A lead system of this nature is described in commonly-assigned U.S. Pat. No. 4,643,201 to Stokes. Similarly, U.S. Pat. No. 5,769,881 to Schroeppel et al. describes a branch assembly that accommodates the selective use of one stylet to position first and second distal fingers of a lead within the right atrium and ventricle, respectively, of the heart. U.S. Pat. No. 5,628,779 to Bomnzin et al. disclose a bifurcated lead having a J-shaped finger locations at a proximal portion of the lead, and an oppositely-shaped distal curved portion. The two curves may be straightened by a stylet during lead deployment. Upon removal of the stylet the lead re-assumes a curved shape, allowing the J-shaped extension to protrude into the right atrial appendage while the distal end of the lead drapes through the tricuspid valve and into the right ventricular apex.

The above-discussed systems discuss lead systems for use in pacing within the right atrium and ventricle. Recently, it has become apparent that pacing in both ventricles can provide important benefits to patients. This is particularly true for patients suffering from heart failure. One investigation has shown that left ventricular pacing should be focused at the site of latest left ventricular activation to create synchronized contractions with right ventricular apical pacing. This location is typically the posterior or posteroinferior base for most patients with chronic LV dysfunction. (Leclercq C, et al. Acute hemodynamic effects of biventricular DDD pacing in patients with end-stage heart failure. J Am Coll Cardiol 1998; 32 (7):1825–31) Pacing electrodes may be implanted deep within the coronary sinus at the ostium of a lateral or posterolateral vein to pace from this location.

Current lead systems for performing big-ventricular pacing utilize two leads, each located within a respective ventricle. This results in some of the disadvantages discussed above. What is needed, therefore, is an improved system for performing big-ventricular pacing that may be used to re-synchronize contractions within the right and left ventricles. Ideally, the system would address the problems associated with multiple-lead pacing systems that are discussed above.

SUMMARY OF THE INVENTION

The present invention provides a left-sided big-furred medical electrical lead that is adapted to be implanted in the cardiac venous system. The inventive lead includes a bifurcated distal portion having first and second elongated members, or fingers. In one embodiment, the first elongated member, or thumb portion, is adapted to be positioned within the coronary sinus or great cardiac vein. This thumb is particularly adapted to be positioned within the coronary sinus near the ostium of the great cardiac vein in a posterolateral position along the base of the left ventricle. The second elongated member, or finger portion of the bifurcated distal tip, may be positioned within a branch vessel of the coronary sinus such as the posterior vein or middle cardiac vein.

According to one aspect of the inventive lead system, the thumb portion may carry at least one electrode for pacing and/or sensing, and may carry additional electrodes for multi-polar pacing applications. Portions of the pacing/sensing electrode may be insulated so that electrical stimulation is only delivered to myocardial tissue, and not to muscle or nerve tissue located posterior to the heart. The finger portion may carry a defibrillator electrode. Additional electrodes may be carried along the lead body for pacing and/or sensing.

In one embodiment of the bifurcated lead system, the finger extends more distally than the thumb portion, and may have a pre-formed canted or formable distal tip. The canted tip helps to guide the finger into the branch vessel toward the apex of the heart. The thumb of the lead system may also include a preformed curvature angling away from the finger. Electrodes carried by the thumb are preferably oriented so that the electrode surfaces will contact the epicardium when the first finger is fully inserted.

The lead system of the current invention may be delivered by use of a guide catheter. During lead delivery, the lead thumb is maintained in a substantially parallel position with the finger using a stiffening member such as a stylet wire that is advanced within a lumen of the lead. In addition to maintaining the parallel position, the stylet adds stiffness to the lead body so it may be easily pushed through a delivery catheter.

In one embodiment, the lumen for receiving the stylet is formed by one or more insulated sets of conductor cables that are loosely twisted about the stylet and that extend from the proximal end of the lead to the distal end of the thumb where they are connected to one or more electrodes. In this embodiment, the lumen provides only enough clearance for the stylet to be removed from, but not re-inserted within, the lumen. This significantly reduces the lead size.

According to another aspect of the invention, the proximal segment of the lead may includes a conductor coil formed of multiple filars of drawn, silver-cored wire. This wire is wound about insulating tubing that carries the twisted cables and stylet. This coil construction aids in the transfer of torque from the proximal end of the lead. The conductor coil may extend from the proximal end of the lead to the bifurcation of the lead distal tip. At the bifurcation, the coil may transition to a smaller, offset, diameter coil.

A cable made from drawn silver-cored wire may be provided to extend from a point at the bifurcation through the insulated core of the finger. At the distal end of the finger, the cable may be joined to a defibrillator coil electrode that extends over the insulated core and proximally along the finger.

In one embodiment, the bifurcated lead is delivered via a catheter having a distal tip advanced within the coronary sinus to a point near the ostia of the posterior or posterolateral and the great cardiac veins. The lead, in a low profile configuration with the thumb maintained substantially parallel to the finger by the stylet, may be advanced through the catheter. Once the distal tip of the lead is aligned with that of the catheter, the proximal end of the lead may be rotated to orient the canted distal tip of the finger toward the ostium of the posterior vein. The finger may then be advanced into the posterior vein until the tip of the thumb becomes aligned with the tip of the catheter. The stylet may then be withdrawn from the thumb as the lead is pushed forward. The curvature of the thumb will direct the thumb away from the finger and into the ostium of the great cardiac vein. After the elongated members have been fully inserted, the catheter may be withdrawn from the body.

According to one method of using the inventive system, the lead may be employed in conjunction with a standard right ventricular pacing and defibrillator lead to deliver big-ventricular pacing and defibrillator therapy. For example, the thumb portion of the bifurcated lead may provide synchronous pacing pulses delivered in conjunction with pacing pulses provided by the lead implanted in the apex of the right ventricle. Similarly, the finger portion of the bifurcated lead may be used to deliver a cardioversion/defibrillator shock across the cardiac tissue located between the finger portion and the defibrillator electrode that is carried by right ventricular lead.

The inventive lead system has several benefits. Because only a single lead is needed to carry both the defibrillator and pacing electrodes to the left-side of the heart, wear caused by leads shifting positions relative to one another may be eliminated. Moreover, the implantation process is simplified by the use of a single lead, reducing the time of implant. Additionally, the two-fingered configuration provides additional stability, allowing the lead to be retained at the desired site of implant. This is important in left-heart applications, since fixation within larger diameter veins such as the coronary sinus is particularly difficult. In many instances, pacing, from the coronary sinus or ostium of the great cardiac vein to stimulate the base of the left ventricle may be better synchronized with the pacing from the right ventricular apex. Because of the improved stability, the pacing electrodes need not be advanced as far into the veins. Other benefits will become apparent to those skilled in the art from the following description and the accompanying drawings.

DETAILED DESCRIPTION OF THE DRAWINGS

Figure 1:
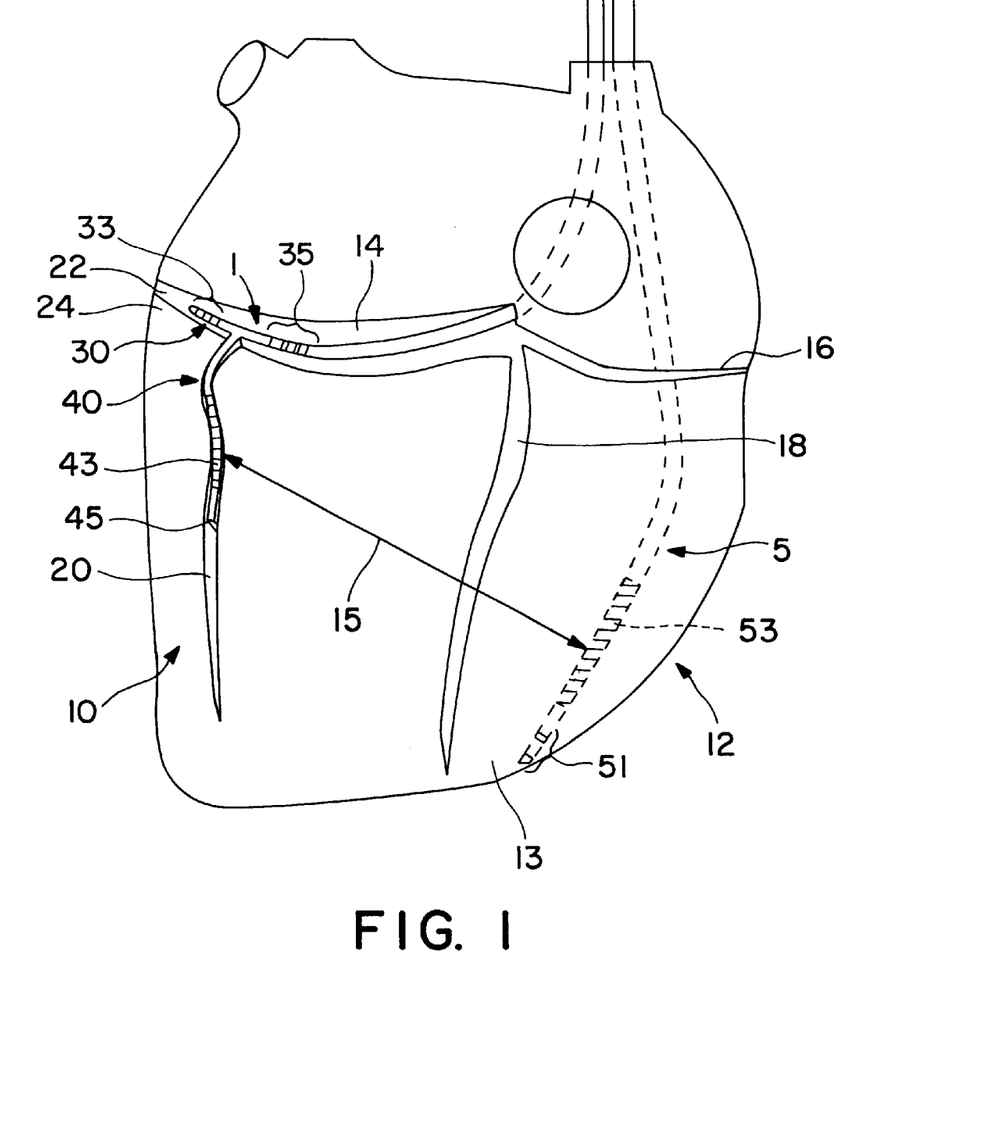
FIG. 1 is a view of the posterior surface of the human heart.

FIG. 1 is a view of the posterior surface of the human heart. This view of the heart shows the coronary sinus 14, the small cardiac vein 16, the middle cardiac vein 18, the posterior vein 20, and the great cardiac vein 22. A first medical electrical lead 5 (shown dashed) may be implanted within the right ventricle 12. This lead may include one or more pacing and/or sensing electrodes such as electrode pair 51. A second distally bifurcated lead 1 is also shown advanced within the coronary sinus 14.

Distally bifurcated lead 1 includes a bifurcated portion including first and second elongated members. The first elongated member may be described as thumb portion 30, whereas the second elongated member may be referred to as finger portion 40. The thumb portion 30, which is shown implanted near the distal end of the coronary sinus 14 proximate to the ostium of the great cardiac vein 22, may carry at least one electrode. FIG. 1 illustrates an exemplary electrode pair 33 for bipolar pacing and/or sensing of the left ventricle. This pacing may be synchronized with pacing and/or sensing of the right ventricle using exemplary electrode pair 51. The thumb portion 30 may carry more than two electrodes for multi-polar pacing. In one embodiment, the length of thumb 30 may range from approximately 1 to 3 cm.

Bifurcated lead further includes the second bifurcated (finger) portion 40, as discussed above. In one embodiment, the length of the finger portion 40 is at least long enough to carry a defibrillator electrode 43 of sufficient length to delivery an effective defibrillator shock. For example, finger portion may range from approximately 4 to 7 cm. Finger portion may further include a canted tip 45 to aid in advancing the finger portion down the selected vein shown in FIG. 1 as the posterior vein 20.

Lead 5 may further include a defibrillator electrode 53. In this instance, a defibrillation pathway exists between the right ventricular defibrillation electrode 53 and the left ventricular defibrillation electrode 43 carried on finger 40 as indicated by arrow 15. This defibrillation pathway 5 includes a large portion of myocardial tissue in a manner that allows the defibrillation threshold to be decreased.

In one embodiment of the invention, one or more of the electrodes of electrode pair 33 includes multiple surfaces to increase the efficiency of the electrode performance. As is known in the art, several factors dictate the performance of a pacing/sensing electrode. For efficient performance, the conductive surface of an electrode should be oriented toward, and make intimate contact with, the epicardial surface of the heart. Efficient performance also relies upon the surface area of the electrode. An electrode having a smaller surface area can generate a given current using less energy than a similar electrode having a larger surface area. In addition, electrical stimulation directed away from the surface of the heart may unintentionally stimulate nerves and muscle tissue. To address these concerns, one embodiment of the invention includes electrodes of electrode pair 33 having a first conductive surface to contact myocardial tissue, and a second insulated surface adapted to face away from the heart.

According to yet another aspect of the invention, lead 1 may include one or more additional electrodes 35 along the elongated lead body to provide additional pacing and/or sensing capabilities.

Figure 2A:
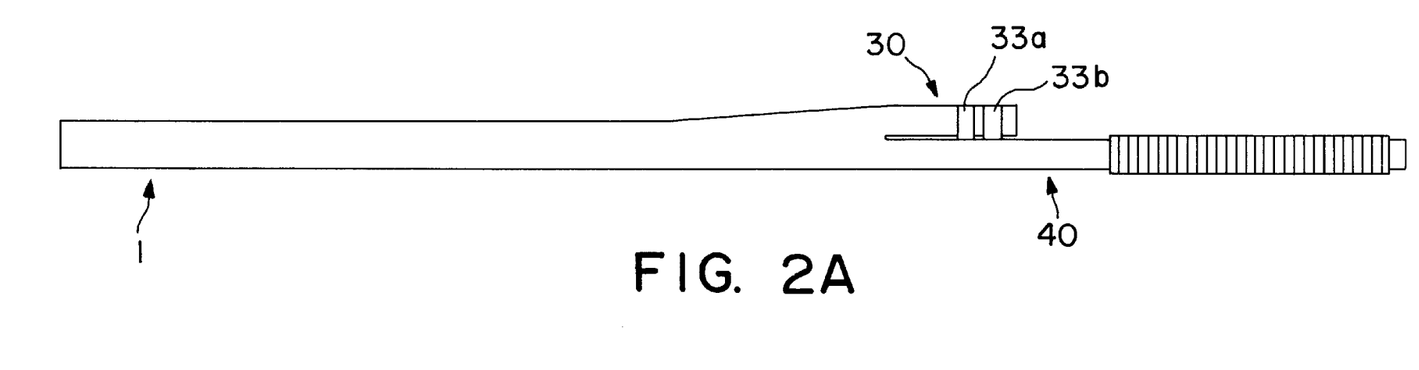
FIG. 2A is a plan view illustrating in more detail the conductive electrode surfaces of one embodiment of the pacing/sensing electrode pair of FIG. 1.

FIG. 2A is a plan view illustrating in more detail the conductive electrode surfaces of one embodiment of the electrode pair 33 shown in FIG. 1. These conductive electrode surfaces 33a and 33b are adapted to face toward the surface of the heart and to provide electrical stimulation to the myocardial tissue. In one embodiment, electrode surfaces 33a and 33b may be made of platinum-iridium alloy with a sintered and platinized surface. These electrode surfaces may each range from approximately 3 to 6 square millimeters. The spacing between the two electrodes may range from approximately 5 to 12 millimeters.

Figure 2B:
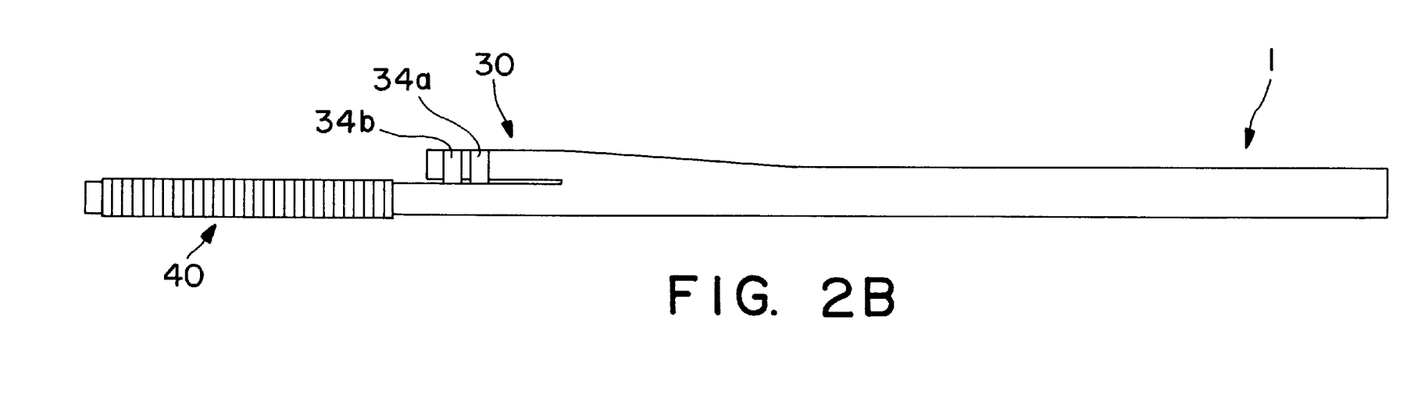
FIG. 2B is a plan view illustrating the insulated electrode surfaces of one embodiment of the pacing/sensing electrode pair.

FIG. 2B is a plan view illustrating the insulated electrode surfaces of one embodiment of the pacing/sensing electrode pair 33. In this embodiment, the portion of the electrodes in electrode pair 33 that are oriented away from the heart, including surfaces 34a and 34b, are provided with an insulation material. This insulation may be any type of biocompatible insulation material that may be extruded over, or adhesively bonded to, the desired portion of the electrodes. This prevents electrical stimulation from being delivered by electrode pair 33 to nerves and other tissue in an inadvertent fashion during pacing of the left ventricle. Because the insulated surface helps decrease the current delivered to the patient's body, this design prolongs the battery life of the attached implantable medical device.

Figure 3:
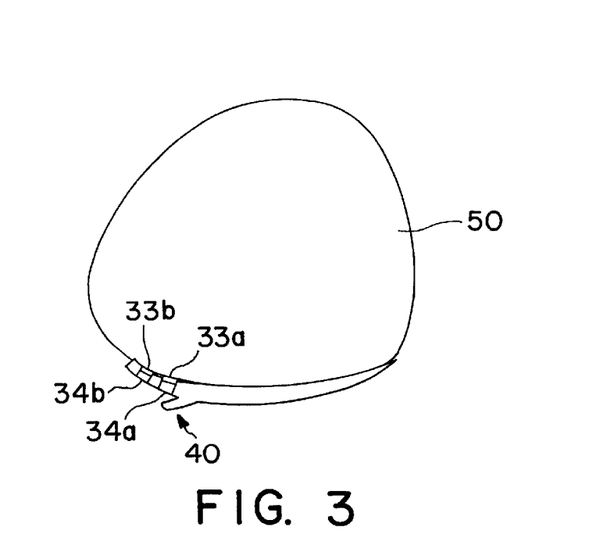
FIG. 3 is a plan view the inventive lead illustrating the manner in which the thumb portion of the lead makes contact with the heart.

FIG. 3 is a plan view of the inventive lead illustrating the manner in which thumb portion 30 makes contact with the heart. The curvature of thumb portion 30 and the dimensions of the vessel maintain conductive electrode surfaces 33a and 33b in close proximity to the heart surface 50 so that optimal pacing efficacy is achieved. The insulated electrode surfaces 34a and 34b are located away from the heart so that adjacent muscle and nerve tissue is not electrically stimulated. In this view, only a proximal portion of finger 40 is shown, with a majority of this structure extending along an axis that is perpendicular to the plane of the paper.

Figure 4:
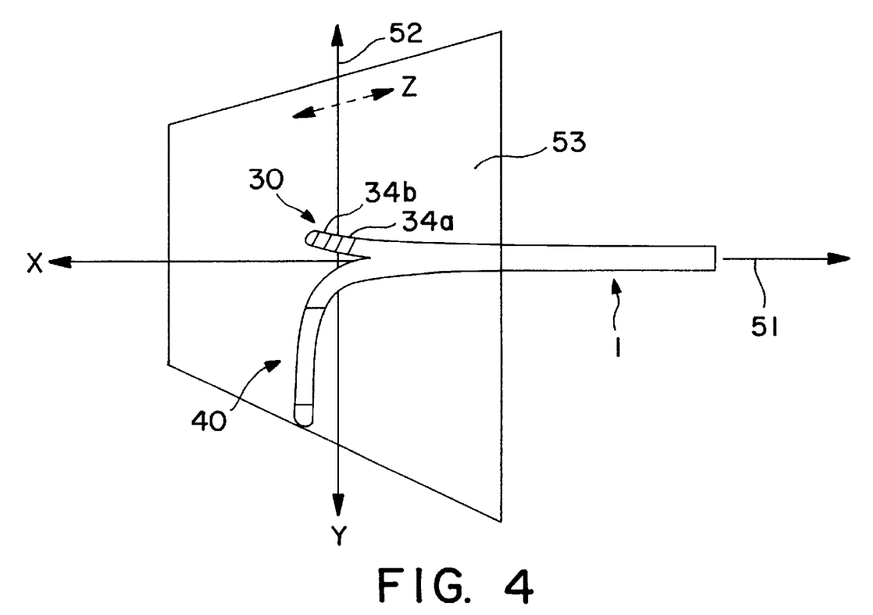
FIG. 4 is a perspective view of one embodiment of the bifurcated lead system.

FIG. 4 is a perspective view of one embodiment of the bifurcated lead system. This view illustrates an X and Y axes 51 and 52, respectively, superimposed over a Z-axis plane 53 which is perpendicular to the plane of the paper. In this view, finger 40 is shown extending substantially along the Y axis. Thumb 30 curves in a direction that is substantially parallel to the Z axis in a plane perpendicular to the paper, and along the curvature of the heart surface. This view includes insulated electrode surfaces 34a and 34b, which, as discussed above, are on the side of lead 1 positioned away from myocardial tissue.

As discussed above, thumb 30 may include a curvature to enable this portion of the lead to better contact the surface of the heart. This curvature also aids is placing the thumb near the ostium of the great cardiac vein 22 (FIG. 1) during lead deployment. Further, this curvature aids in maintaining the lead at a stable location with the vascular system when the lead is deployed at a location wherein the vessel dimensions are larger than would otherwise be needed to hold the lead in place.

While the curvature of the thumb 30 provides important benefits, it makes the inventive lead system more challenging to deploy. According to one aspect of the invention, a stiffening member such as a stylet may be provided within lead to maintain thumb 30 in a straightened configuration that is substantially parallel to finger 40. This stiffening member is utilized to enable the lead to be advanced within a vessel. For example, the stiffening member may be employed to straighten thumb 30 so that the lead may be advanced within an inner lumen of a guide catheter that has been navigated to the proximity of the implant site.

In one embodiment, the stiffening member is a removable-only stylet. According to this aspect of the invention, the lead lumen housing the stylet does not include enough clearance to allow the stylet to be re-inserted within the lead after it has once been removed. For example, this lumen may be defined by elongated structures such as cables or conductors that are twisted or wound about the stylet. A lumen of this nature allows the lead dimensions to be as small as possible.

Figures 5, 7, 8:
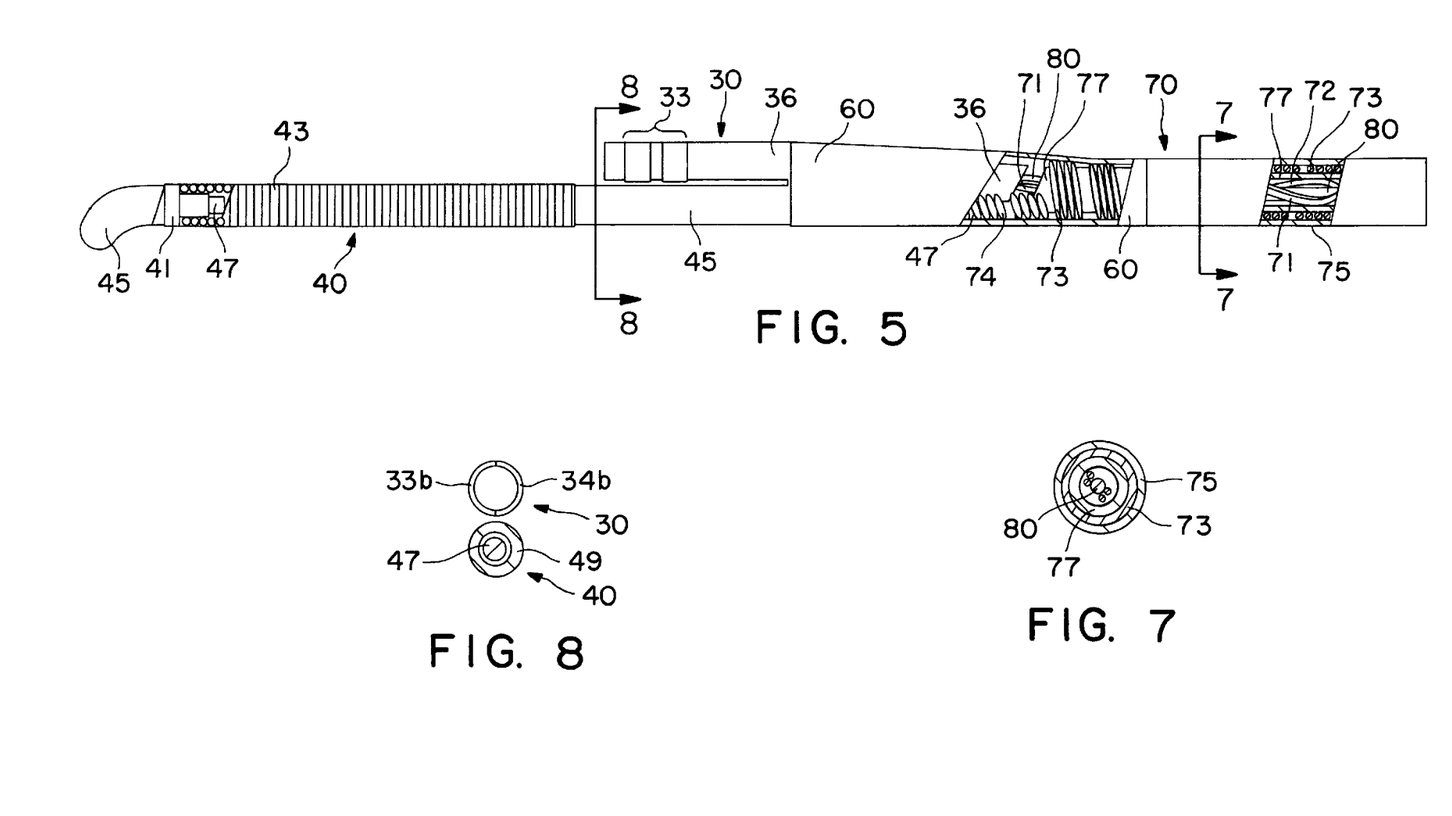
FIG. 5 is a partially cutaway side view of one embodiment of the inventive bifurcated lead system including a stiffening member.
FIG. 7 is a cross-section view of lead body at line 7—7 of FIG. 5.
FIG. 8 is a cross-section view of the distal end of lead at line 8—8 of FIG. 5.

FIG. 5 is a partially cutaway side view of one embodiment of the inventive bifurcated lead system including a stiffening member, which may be a stylet 80. The lead body 70 includes two sets of insulated conductor cables 71 and 72, which are loosely twisted about stylet 80. These sets of conductor cables each extends into thumb 30 to electrically couple to a respective one of the electrodes in the electrode pair 33. The conductor cables are twisted about the stylet leaving only enough clearance for the stylet to be removed from the lumen, but not easily re-inserted within the lumen. The stylet 80 extends from the proximal end of the lead body to the distal end of the thumb portion 30 to maintain the thumb substantially parallel with finger 40 as is depicted in FIG. 5. The stylet also serves to add stiffness to the lead body so it may be easily pushed through a delivery catheter. When the stylet is removed, thumb 30 relaxes into its preformed curvature, away from the finger 40.

As discussed above, wires comprising cables 71 and 72 may each be insulated with a jacket of fluoropolymer. According to one aspect of the lead system, the cables and stylet may be enclosed within an inner tubing of insulation 77. In one embodiment of the invention, the diameter of this inner assembly 36 comprised of stylet 80, twisted insulated pairs of cables 71 and 72, and insulation tubing 77 may range from approximately 0.040 to 0.060 inches.

A conductor coil 73, which may be made from multiple filars of drawn silver-cored wire or another type of conductive material, may also be provided about insulating tubing 77. This coil construction aids in the transfer of torque from the proximal end to the distal end of the lead. Conductor coil 73 may extend from the proximal end of the lead into bifurcation sleeve 60. Within the bifurcation sleeve, the conductor coil may transition to an offset smaller diameter coil 74 where it is joined to a conductor cable 47. Conductor cable 47 is, in turn, electrically coupled to defibrillation electrode 43 at the distal end of finger 40. This coupling may be performed by means of a weld core crimp sleeve 41. In this embodiment, the cable may be crimped within the lumen of the crimp sleeve 41. The end of the electrode coil may be mounted over the crimp sleeve and welded to the shoulder of the sleeve.

Lead 1 includes an outer insulation 75 that may be formed of any of the biocompatible insulative materials adapted for use in implantable medical leads. In one embodiment of the lead, the diameter of the main body 70 of the lead as defined by the outer insulation may range from approximately 0.064 to 0.078 inches. Outer insulation 75 extends from the proximal end of lead 1 and into bifurcation sleeve 60.

Finger 40 is comprised of an insulation tubing that is joined to the distal end of the bifurcation sleeve 60, and that houses the cable conductor 47. As discussed above, finger 40 may include one or more electrodes. In the embodiment of FIG. 5, finger 40 includes defibrillation electrode 43, which may have an outer diameter ranging from approximately 0.028 to 0.050 inches, and a length ranging from approximately 3 to 5 cm. In one embodiment, finger 40 further includes a canted distal tip 45 to aid in positioning of finger 40 during lead deployment.

Figure 6A:
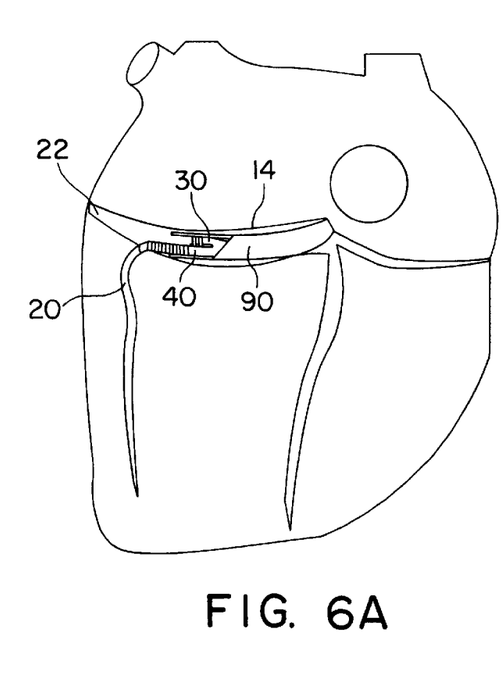
FIGS. 6A through 6D illustrate one manner of deploying the inventive lead system using a delivery catheter.
Figure 6B:
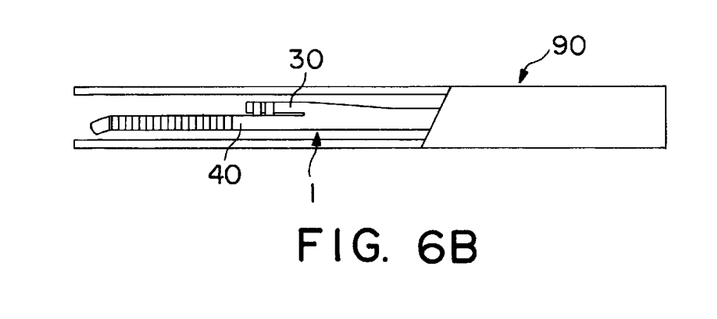
Figures 6C, 6D:
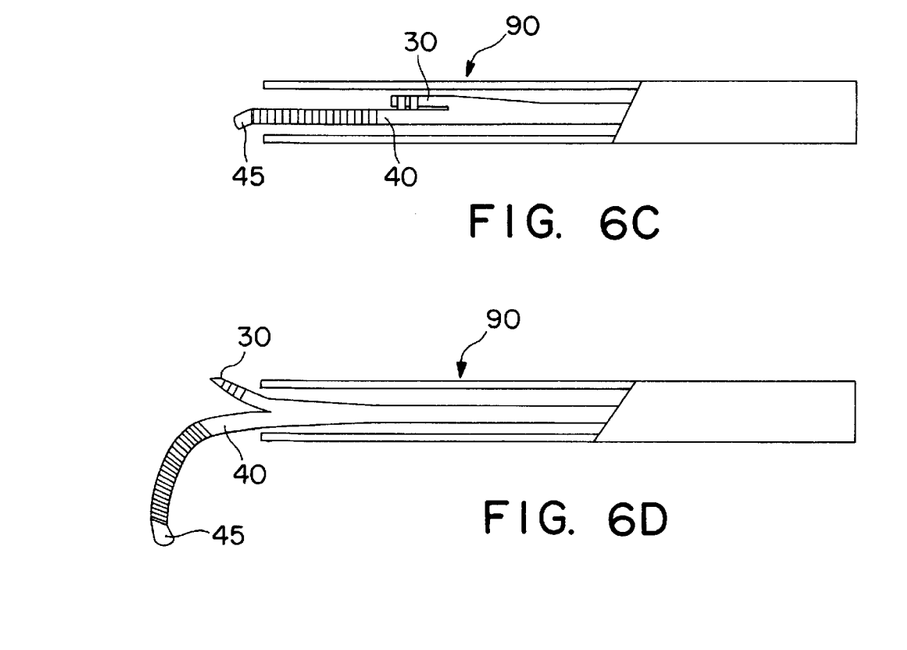

FIGS. 6A through 6D illustrate one manner of deploying the inventive lead system via a delivery catheter 90. Using this method of deployment, catheter 90 is positioned so that the catheter distal tip is located within the coronary sinus 14 near the ostia of two converging venous structures. FIG. 6A illustrates the catheter distal tip being positioned at the ostia of the posterior vein 20 and the great cardiac vein 22, for example. As shown in FIG. 6B, before the lead is advanced beyond the distal tip of catheter 90, the lead is in a low-profile configuration. The thumb 30 is maintained in a substantially parallel position with finger 40 by the stylet 80 (not shown in FIG. 6B.) Once the distal tip of the lead is aligned with that of the catheter, the proximal end of the lead may be rotated to orient the canted distal tip 45 toward the ostium of the posterior vein. The canted distal tip may then be advanced beyond the catheter distal tip and directed into the posterior vein, as illustrated by FIGS. 6A and 6C. Finger 40 may then be pushed into the posterior vein until the tip of the thumb becomes aligned with the tip of the catheter. At this point, the stylet may be withdrawn from the thumb 30 as the lead is pushed forward. This is depicted by FIG. 6D.

According to one aspect of the invention, a portion of the bifurcation sleeve 60 extends into the thumb and may be preformed to bend away from the first finger 40. This curvature of thumb 30 aids in directing the thumb away from finger 40 and into a predetermined vascular structure such as the ostium of the great cardiac vein 22 during lead deployment. When the lead fingers have been fully positioned within the vascular system, the catheter may be withdrawn over the lead body. A splittable or pealable catheter may be used to allow the catheter to be withdrawn over the lead connector if the connector is not low-profile.

FIG. 7 is a cross-section view of lead body 70 at line 7—7 of FIG. 5. This view illustrates outer insulation 75 surrounding conductor coil 73 and insulation tubing 77. Within the inner lumen of insulation tubing 77, the sets of insulated conductor cables 71 and 72 are shown twisted about stylet 80.

FIG. 8 is a cross-section view of the distal end of lead 1 at line 8—8 of FIG. 5. This view illustrates thumb 30 held in an in-line position with finger 40 as would be desirable during lead deployment. Thumb 30 is shown to include at least one electrode having a conductive surface 33b and a surface 34b that is insulated in a manner discussed above. This view further illustrates insulation tubing 49 surrounding cable conductor 47 of finger 40. In one embodiment, the outer diameter of insulation tubing may range from approximately 0.028 to 0.040 inches.

Many modifications to above-described inventive lead system are possible within the scope of the present invention. For example, the dimensions of the system may be modified to accommodate the variability in patients' coronary venous anatomy. Additionally, the sites of infarction may dictate alternative placement of the lead system. For example, although the description discusses placement of the lead at the convergence of the posterior and great veins, placement may instead occur where the middle cardiac vein 18 converges with the coronary sinus. Other locations for the defibrillation electrode might be found in other cardiac veins that descend from the coronary sinus down the posterior or lateral surface of the left ventricle.

Other possible modifications for the lead system involves electrode placement. For instance, the sensing/pacing electrodes may be included on finger 40 instead of thumb 30, with thumb 30 being used merely to stabilize lead location. Alternatively, the pacing/sensing electrodes could be moved to a predetermined location along the main body portion 70 of the lead. In another embodiment, defibrillation electrode may be moved to thumb 30. In this design, thumb may be increased in length to equal, or even exceed, the length of finger 40. This both accommodates the alternative electrode placement and provides more reach along the length of the coronary sinus and great cardiac vein. In addition, electrodes may be added or deleted. As noted above, more than two sensing/pacing electrodes may be included on the lead in any of the aforementioned positions. Additional modifications within the scope of the invention will be apparent to those skilled in the art from the foregoing description and the accompanying drawings.

What is claimed is:

1. A medical electrical lead to be implanted within a heart, comprising:
   an elongated lead body having a proximal portion and a distal portion;
   a first elongated member coupled to the distal portion, the first elongated member adapted to be positioned within the coronary sinus of the heart; and
   a second elongated member coupled to the distal portion, the second elongated member adapted to be positioned within a branch vein of the coronary sinus of the heart.

2. The lead of claim 1, wherein the first elongated member includes at least a first electrode.

3. The lead of claim 2, wherein the second elongated member includes at least a second electrode.

4. The lead of claim 3, wherein the at least second electrode is a defibrillation coil adapted to deliver cardioversion/defibrillation stimulation to the heart.

5. The lead of claim 4, wherein the at least first electrode is adapted to deliver pacing pulses.

6. The lead of claim 5, and further including a third electrode carried on the first elongated member to deliver multi-polar pacing pulses between the first and third electrodes.

7. The lead of claim 3, wherein the second elongated member includes a canted distal tip.

8. The lead of claim 7, wherein the canted distal tip is formed to allow the second elongated member to more readily enter the branch vein.

9. The lead of claim 3, wherein the first elongated member includes a pre-formed distal tip.

10. The lead of claim 1, and further including:
    a lumen extending the length of the elongated body and extending into at least a portion of the first elongated member; and
    a stiffening member adapted to be advanced within the lumen.

11. The lead of claim 10, wherein the first elongated member includes a pre-formed bend, and wherein insertion of the stiffening member into the lumen maintains the second elongated member in substantially parallel alignment with the second elongated member.

12. The lead of claim 10, wherein the lumen is formed by twisted conductor cables.

13. The lead of claim 12, wherein the lumen is sized to allow the stiffening member to be removable-only.

14. The lead of claim 2, wherein predetermined ones of the at least first electrode has a portion that is insulated.

15. The lead of claim 14, wherein the portion that is insulated is positioned to be in contact with tissue that is of a type other than myocardial tissue.

16. The lead of claim 3, wherein the elongated lead body includes at least one electrode.

17. A method of providing treatment to a patient using a lead having an elongated body coupled to a bifurcated distal tip, the bifurcated distal tip including a first elongated member and a second elongated member, comprising the methods of:

a.) delivering the lead to a predetermined site of implant in the coronary sinus of a heart;

b.) positioning the bifurcated distal tip of the lead in a predetermined orientation;

c.) withdrawing a stiffening member from within a lumen of the lead that extends into at least a portion of the first elongated member, wherein the withdrawing method allows the first elongated member to be placed with a first vessel, and the second elongated member to be placed in a second vessel.

18. The method of claim 17, wherein the first vessel is the coronary sinus.

19. The method of claim 17, wherein the first vessel is the great cardiac vein.

20. The method of claim 17, wherein the second vessel is the posterior vein.

21. The method of claim 17, wherein the second vessel is the middle cardiac vein.

22. The method of claim 17, wherein method a.) includes the method of advancing a guide catheter to the predetermined site of implant.

23. The method of claim 22, wherein method a.) further includes the method of advancing the lead through a lumen of the guide catheter until the bifurcated distal tip of the lead is proximate a distal end of the guide catheter.

24. The method of claim 23, wherein a distal tip of the second elongate member includes a pre-formed bend, and wherein method b.) includes the methods of:

b1.) positioning the pre-formed bend in a predetermined orientation with respect to an ostium of the second vessel; and b2.) advancing the second elongated member from the guide catheter into the second vessel until a distal tip of the first elongated member is substantially aligned with a distal tip of the guide catheter.

25. The method of claim 24, wherein the lead includes a stiffening member extending from a proximal end of the lead into at least a portion of the first elongate member, and wherein method c.) includes the method of advancing the first elongated member from the guide catheter into the first vessel while withdrawing the stiffening member.

26. The method of claim 25, wherein the first elongated member includes a pre-formed bend, and method c.) allows the first elongated member to assume the pre-formed bend to enter the first vessel.

27. The method of claim 26, and further including the methods of:

providing a first defibrillation coil on the second elongated member;

providing a second lead located within the right ventricle of the patient, the second lead carrying a second defibrillation coil;

coupling the first and second leads to an implantable pulse generator; and delivering electrical stimulation between the first and the second defibrillation coils to cardiovert/defibrillate the patient's heart.

28. The method of claim 27, and further including the methods of: providing at least one pacing electrode on the first elongated member; and delivering pacing pulses via the at least one pacing electrode.

29. The method of claim 28, and further including the methods of: providing at least two pacing electrodes on the first elongated member; and delivering pacing pulses between a predetermined pair of the at least two pacing electrodes.

30. The method of claim 27, wherein ones of the at least one pacing electrode has a predetermined insulated portion and a predetermined non-insulated portion, and further including the method of positioning the non-insulated portion of the ones of the at least one pacing electrode to be proximate to cardiac tissue.

* * * * *